(12) United States Patent
Ishikawa (10) Patent No.: US 6,608,675 B1
(45) Date of Patent: Aug. 19, 2003

(54) METHOD FOR VISUALIZING HIGHER-ORDER STRUCTURE OF TRANSPARENT OPTICAL POLYMER MOLDING

(75) Inventor: Ichiro Ishikawa, Yokosuka (JP)

(73) Assignee: Nissan Arc, Ltd., Kanagawa-Prefecture (JP)

( * ) Notice: Subject to any disclaimer, the term of this patent is extended or adjusted under 35 U.S.C. 154(b) by 0 days.

(21) Appl. No.: 09/717,283

(22) Filed: Nov. 22, 2000

(30) Foreign Application Priority Data

Aug. 28, 2000 (JP) ........................................ 2000-257100

(51) Int. Cl.⁷ ............................................. G01N 21/00
(52) U.S. Cl. ................................. 356/237.1; 356/239.1; 356/239.2
(58) Field of Search ........................... 356/237.1, 237.2, 356/237.3, 237.4, 237.5, 237.6, 239.1, 239.2, 239.7, 239.8; 369/44.23, 100, 284; 250/562–563, 572

(56) References Cited

U.S. PATENT DOCUMENTS

| | | | | |
|---|---|---|---|---|
| 4,954,723 A | * | 9/1990 | Takahashi et al. | ....... 356/237.1 |
| 5,098,191 A | * | 3/1992 | Noguchi et al. | ......... 356/237.1 |
| 5,200,948 A | * | 4/1993 | Goldberg et al. | ........... 369/284 |
| 5,208,801 A | * | 5/1993 | Finegan | ...................... 369/284 |
| 5,268,735 A | * | 12/1993 | Hayashi | .................... 356/237.1 |
| 5,715,051 A | * | 2/1998 | Luster | ....................... 356/237.1 |
| 5,726,748 A | * | 3/1998 | Morris | ..................... 356/237.1 |
| 6,396,579 B1 | * | 5/2002 | Hayamizu et al. | ....... 356/239.7 |

FOREIGN PATENT DOCUMENTS

| | | | |
|---|---|---|---|
| JP | 02289943 | * | 11/1990 |
| JP | 04157638 | * | 5/1992 |

OTHER PUBLICATIONS

Ashida et al. *Structure and Properties of Epoxy Resins Modified with Acrylic Particles*, Journal of Applied Polymer Science, vol. 74, 2955–2962 (1999).

* cited by examiner

Primary Examiner—Frank G. Font
Assistant Examiner—Sang H. Nguyen
(74) Attorney, Agent, or Firm—Sughrue Mion, PLLC

(57) ABSTRACT

Higher-order structure in the transparent optical polymer molding such as CD, DVD is enabled to be visualized and observed non-destructively and non-contactingly in a wide range of a microscopic level to a macroscopic level by applying light with specific wavelength to the transparent optical polymer molding from an incident optical system, and visualizing light with specific wavelength selected among a reflected wave and/or a transmitted wave of the light applied to the transparent optical polymer molding through an outgoing optical system.

11 Claims, 10 Drawing Sheets

METHOD FOR VISUALIZING HIGHER-ORDER STRUCTURE OF TRANSPARENT OPTICAL POLYMER MOLDING

BACKGROUND OF THE INVENTION

1. Field of the Invention

This invention relates to a method for visualizing higher-order structure of a transparent optical polymer molding suitable to visualize the higher-order structure such as a shear oriented layer, a spherulite and the like formed in thin disc-shaped transparent optical polymer moldings such as a compact disc (CD), a digital versatile disc (DVD) or so, and the transparent optical polymer molding in shapes of optical parts such as a lens, a prism or so made of high molecule substances in a wide region ranging from a microscopic level to a macroscopic level.

2. Description of the Prior Art

In recent years, the thin disc-shaped transparent optical polymer moldings such as a CD, a DVD and the like have been widely used as a high capacity recording medium instead of the conventional magnetic tape (DAT) and the magnetic disc (FD).

Figure 10:
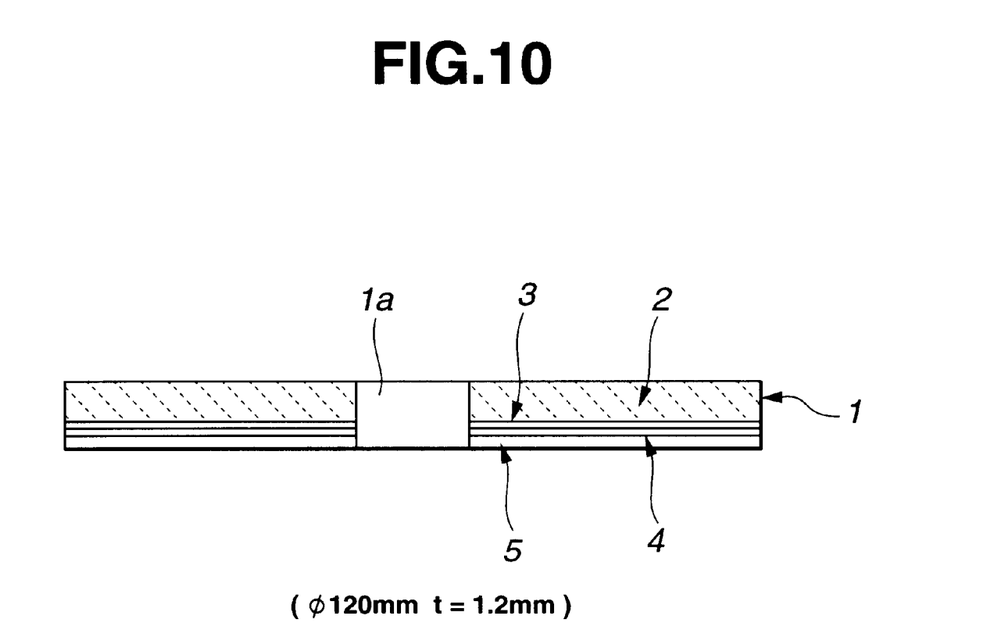
FIG. 10 is a vertical sectional view illustrating an example of structure of the general CD-ROM.

FIG. 10 is a vertical cross-sectional view illustrating the basic sectional structure of the transparent optical polymer molding of this kind (CD-ROM), a reading surface is shown on the upper side and a labelling surface is on the lower side in FIG. 10.

The transparent optical polymer molding (CD-ROM) 1 has a truly round shape with a diameter of 120 mm and a thickness of 1.2 mm (occasionally 0.6 mm×2) typically, and is formed with a center hole 1a. The CD-ROM 1 is laminately formed with a polymer base (pit/land) 2, a reflecting layer (Aluminium layer) 3, a lacquer layer 4 and a printing layer 5 toward the labelling surface from the reading surface side.

In the transparent optical polymer molding of this kind, stable mouldability with high quality and high productivity are required in the injection moulding process, and it is required to meet, for example, the following demands that a) the thickness of the product does not vary widely;

b) birefringence of the product is not large;

c) a large amount of warp does not appear in the product;

d) pattern stability of pits is secured; and e) deformation or cracks are not produced in processes other than moulding, during the transportation, the strage and the application.

Therefore, it has been performed to enable advance examination of the higher-order structure such as the shear oriented layer or the spherulite produced in the transparent optical polymer moldings made of high molecule substances in order to carry out stable moulding of such the transparent optical polymer moldings with high quality, and several testing methods have been introduced, such as a polarized light transmission method, a photoelastic method, an interference method, a birefringence method, an FT-IR method, an ultrasonic method and so.

Additionally, some of these testing methods are described in Mechanical Engineer's Handbook (JSME, Section A4, chapter 10, pp.152–154, New Edition, Second Printing, May 15, 1988).

However, the observation of the structure is mainly carried out in the microscopic region in the afore-mentioned conventional methods and there is a problem in that it is difficult to observe the whole structure of the transparent optical polymer moldings macroscopically in most cases. Accordingly, it becomes a subject to enable the observation of the higher-order structure of the transparent optical polymer moldings for the large sample such as the CD-ROM and the DVD in a wide region ranging from the microscopic level to the macroscopic level without destruction nor contact.

SUMMARY OF THE INVENTION

This invention is made in view of the aforementioned subject, and it is an object to provide a method for visualizing higher-order structure of a transparent optical polymer molding which is possible to observe the higher-order structure such as the shear oriented layer, the spherulite or so produced in the transparent optical polymer moldings made of high molecule substances in the wide region ranging from the microscopic level to the macroscopic level, is possible to know the influence on the mouldability (moulding trouble, residual strain, internal stress and so), the aging and/or degradation (relaxation phenomenon, thermal hysteresis, environmental degradation and so), the memory function or the like without damaging nor breaking the polymer materials in itself, and possible to estimate the physical and mechanical properties of the transparent optical polymer moldings.

The method for visualizing the higher-order structure of the transparent optical polymer molding according to this invention is characterized by comprising the steps of applying light with specific wavelength to the transparent optical polymer molding from an incident optical system, and visualizing light with specific wavelength selected among a reflected wave and/or a transmitted wave of the light applied to the transparent optical polymer molding from the incident optical system by an outgoing optical system.

The method according to an embodiment of this invention is characterized in that the transparent optical polymer molding is a product selected from the group consisting a disc, a flat lens, a prism and an optical filter formed from transparent resin such as polycarbonates, poly(ether sulfone), poly(ethylene terephthalate), polyolefine resins, acrylic resins, epoxy resins, and a mixture, alloy and composite material of these resins.

Further, the method according to another embodiment of this invention is characterized by using a light source which is possible to apply ultraviolet rays or near ultraviolet rays, such as a mercury lamp, an incandescent lamp, a black-light, a tungsten halogen lamp, a xenon lamp, an eximer UV lamp, a UV laser and so, as a light source of the incident optical system.

Furthermore, the method according to the other embodiment of this invention is characterized in that the incident optical system is provided with an incident-side filter to be passed through with light of which wavelength is not more than 400 nm.

The method according to the other embodiment of this invention is characterized by supporting the transparent optical polymer molding on a plane directly or multiple points, or in a suspended state.

The method according to the further embodiment of this invention is characterized in that the outgoing optical system is provided with an outgoing side-filter for selecting the light with the specific wavelength among the light reflected and/or transmitted from the transparent optical polymer molding, and the outgoing-side filter is passed through with light of which wavelength is in a range of 200 to 800 nm.

Furthermore, the method according to the other embodiment of this invention is characterized by providing an optical imaging system, an image pickup device, an image processing device and an image display device to the outgoing optical system.

DETAILED DESCRIPTION OF THE INVENTION

Figure 1A:
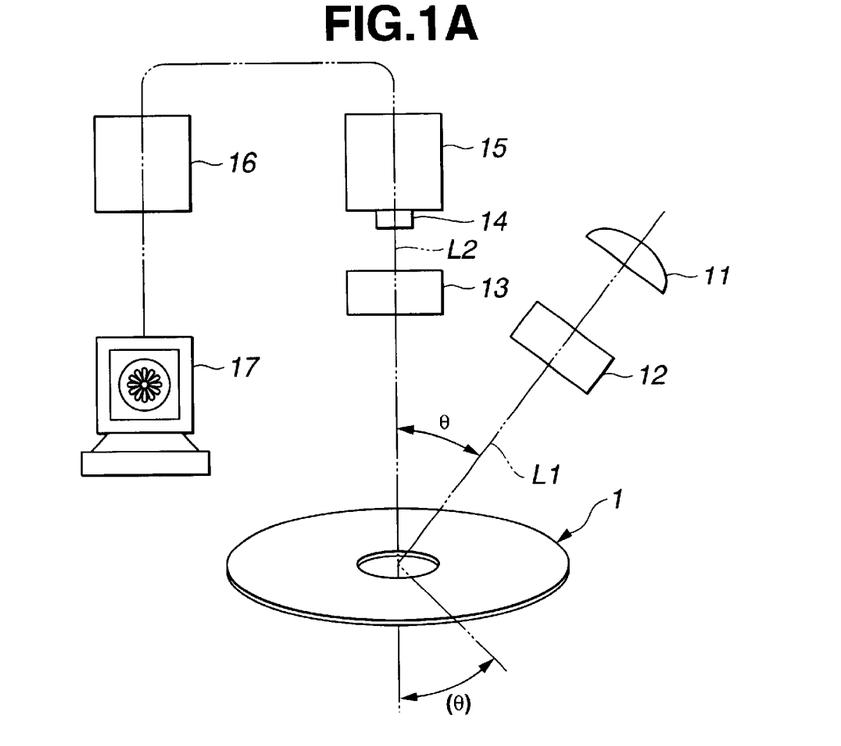
FIG. 1A is a block diagram illustrating an example of the basic formation of the apparatus to be used in the method for visualizing the higher-order structure of the transparent optical polymer molding according to this invention.

An embodiment of the method for visualizing the higher-order structure of the transparent optical polymer molding according to this invention is shown in FIG. 1A, and an apparatus may be used in this embodiment, which is provided with an incident optical system (light source 11, incident-side wavelength 12) for applying light $L_1$ with (first) specific wavelength to the thin-disc shaped transparent optical polymer molding 1 such as a CD, a DVD or the like made of high molecule substances, and an outgoing optical system (outgoing-side filter 13, optical imaging system 14) for visualizing light $L_2$ with (second) specific wavelength selected after going out from the transparent optical polymer molding 1. The higher-order structure of the transparent optical polymer molding 1 is visualized by selecting the light $L_2$ with the (second) specific wavelength among the reflected wave and/or the transmitted wave of the light $L_1$ with the (first) specific wavelength applied against the transparent optical polymer molding 1.

Figure 1B:
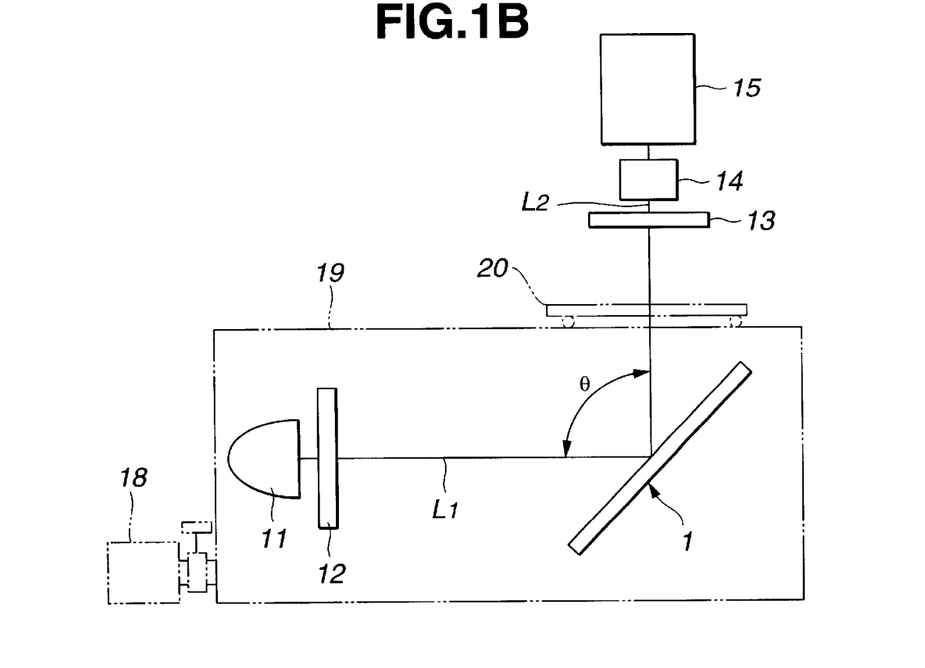
FIG. 1B is a block diagram illustrating another example of the basic formation of the apparatus to be used for the visualizing method according to this invention.

Further, another embodiment of the method for visualizing the higher-order structure of the transparent optical polymer molding according to this invention is shown in FIG. 1B, and a case is shown in this embodiment where the angle between the light $L_1$ with the (first) specific wavelength applied from the incident optical system and the light $L_2$ with the (second) specific wavelength reflected by the transparent optical polymer molding 1 is θ. The higher-order structure of the transparent optical polymer molding 1 is visualized by selecting the light $L_2$ with the (second) specific wavelength among the reflected wave and/or the transmitted wave of the light $L_1$ with the (first) specific wavelength applied to the transparent optical polymer molding 1.

Figure 2:
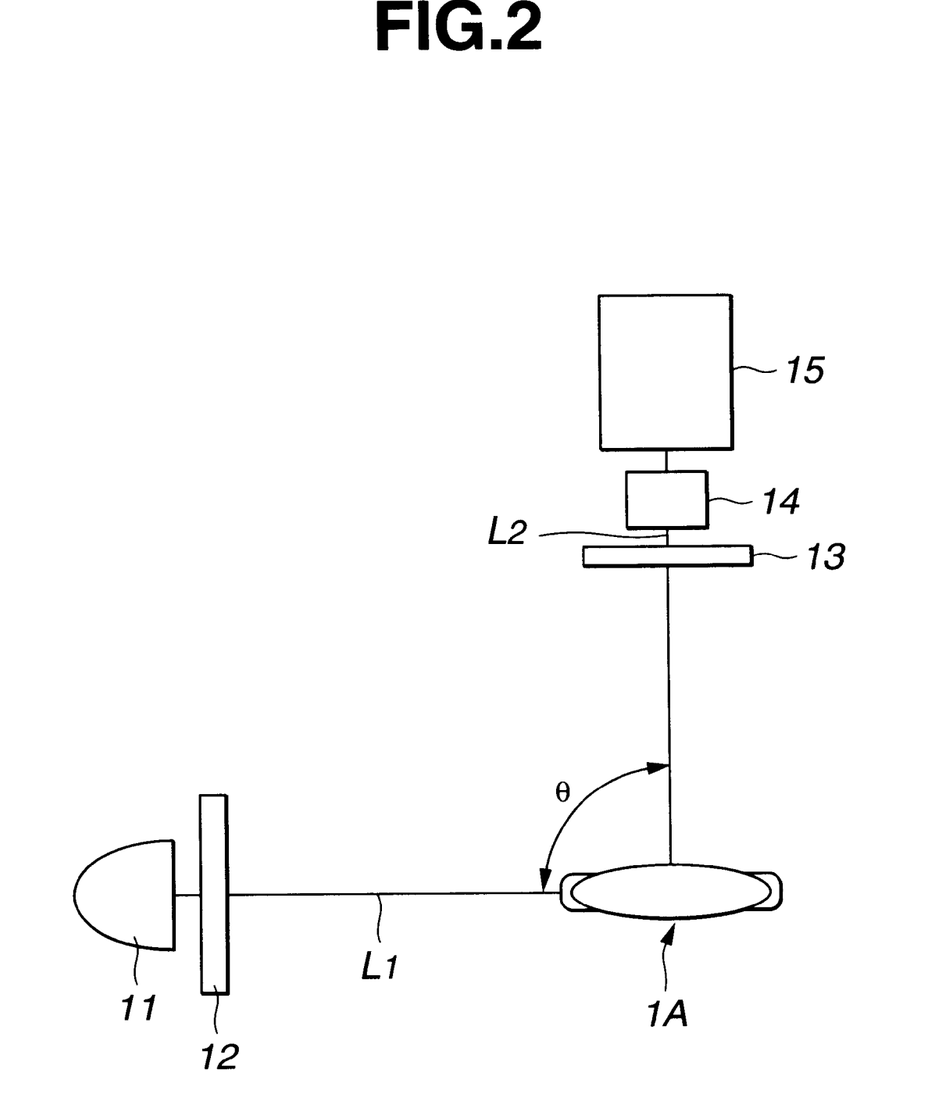
FIG. 2 is also a block diagram illustrating the other example of the basic formation of the apparatus to be used for the visualizing method according to this invention.

Furthermore, the other embodiment of the method for visualizing the higher-order structure of the transparent optical polymer molding according to this invention is also shown in FIG. 2. In this embodiment, the light $L_1$ with the specific wavelength is applied to the transparent optical polymer molding 1A in a shape of optical parts such as a flat lens, a prism or the like made of high molecule substances at an illuminating angle of θ against the normal line from the incident optical system. Also in this case, the higher-order structure of the transparent optical polymer molding 1A is visualized by selecting the light $L_2$ with the (second) specific wavelength among the reflected wave and/or the transmitted wave of the light $L_1$ with the (first) specific wavelength applied to the transparent optical polymer molding 1A.

In an embodiment of this invention, the transparent optical polymer molding 1 or 1A may be formed from raw materials selected from transparent resins such as polycarbonates, poly(ether sulfone), poly(ethylene terephtalate), polyolefine resins, acrylic resins, epoxy resins and so on, or various high molecule substances such as a mixture, an alloy and composite materials of the aforementioned resins.

The light source 11 of the incident optical system may be used by selecting it among various light sources possible to apply ultraviolet rays or near ultraviolet rays, such as a mercury lamp, an incandescent lamp, a black-light, a tungsten halogen lamp, a xenon lamp, an eximer UV lamp, a UV laser and the like.

The incident optical system is provided with the incident-side filter 12 in order to apply the light $L_1$ with the specific wavelength to the transparent optical polymer molding 1 or 1A. In this time, it is desirable to use a filter to be passed with light of which wavelength is not more than 400 nm as the incident-side filter 12. When the wavelength of the light $L_1$ passed through the incident-side filter 12 is longer than 400 nm, it is not desirable because the visualization of the higher-order structure in the transparent optical polymer molding 1 or 1A is apt to be difficult.

The other side, in a case where a filter of which wavelength range is not more than 200 nm as the incident-side filter 12, the light with wavelength in this range is absorbed in air and attenuated, therefore it is necessary to use the embodiment shown with two-dot chain lines in FIG. 1B.

In the apparatus shown in FIG. 1B, it is necessary to install the transparent optical polymer molding 1 and the incident optical system (light source 11, incident-side filter 12) for applying the light $L_1$ with the specific wavelength (range of vacuum ultraviolet rays: UV-V, wavelength range of not more than 200 nm) to the transparent optical polymer molding 1 in a vacuum chamber 19 shown with two-dot chain lines which is possible to be made vacuous by evacuating with vacuum devices 18. In this case, the vacuum chamber 19 is attached with a window pane 20 (substance which does not cause the remarkable absorption in a wavelength range of 200 to 800 nm, such as quartz glass, for example) to be passed through with the light $L_2$, through a vacuum seal (seal which does not affect the wavelength in the range of 200 to 800 nm). In this manner, the higher-order structure of the transparent optical polymer molding 1 is visualized by selecting the light $L_2$ with the specific wavelength among the reflected wave and/or the transmitted wave of the light $L_1$ with the specific wavelength (UV-V) applied to the transparent optical polymer molding 1. In this case, it is not always necessary to set up the optical path of the light $L_2$ in a vacuum, and it may be set up in air so long as the wavelength range of 200 to 800 nm is not influenced.

Figure 3A:
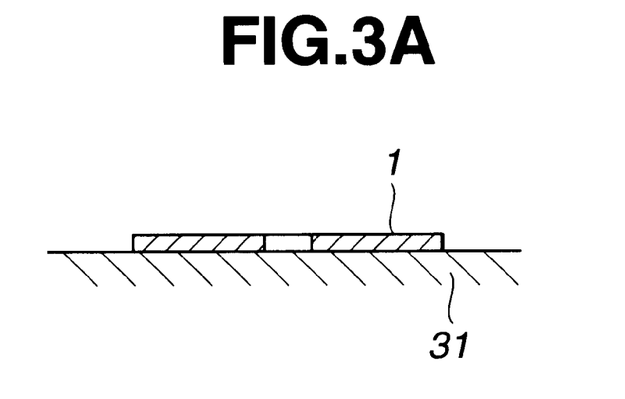
FIGS. 3A, 3B, and 3C are explanatory drawings exemplifying supported states of the transparent optical polymer molding formed in a disc or flat-plate like shape.
Figure 3B:
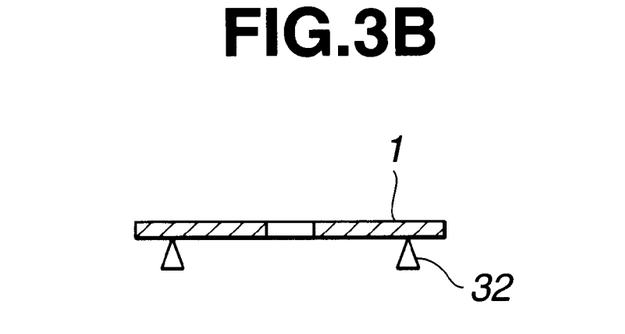
Figure 3C:
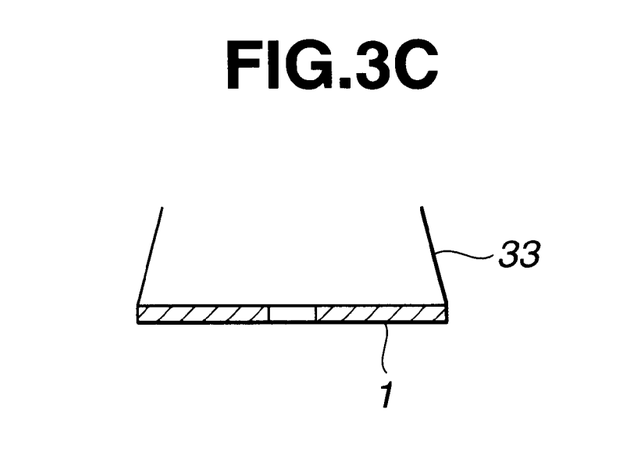

The transparent optical polymer molding 1 or 1a may be supported directly on a plane support member 31 as shown in FIG. 3A, or may be held on multiple supports 32 with pointed top ends as shown in FIG. 3B. Furthermore, the transparent optical polymer molding 1 may be also supported suspendedly by a suspensory support member 33 as shown in FIG. 3C.

The outgoing optical system is provided with the outgoing-side filter 13 for selecting the light $L_2$ with the specific wavelength among the reflected wave and/or transmitted wave of the light $L_1$ applied on the transparent optical polymer molding 1, and it is desirable to use a filter to be passed through W with light of which wavelength is in a range of 200 to 800 nm, further preferable in a range of 200 to 650 nm as the outgoing-side filter 13. In this time, the visualization of the higher-order structure in the transparent optical polymer molding 1 becomes difficult to be carried out satisfactorily if the wavelength of the light $L_2$ passed through the outgoing-side filter 13 is shorter than 200 nm, and it is not desirable because the visualization is apt to be difficult also in a case where the wavelength of the light $L_2$ passed through the outgoing-side filter 13 is longer than 800 nm.

Furthermore, the outgoing optical system may be provided with an optical imaging system 14, an image pickup device 15, an image processing device 16, and image display device 17 and so on, for visualizing the light $L_2$ with the specific wavelength selected by the outgoing-side filter 13, and it is possible to use the conventional devices adopted widely in general machinery as the afore-mentioned respective devices.

DESCRIPTION OF THE PREFERRED EMBODIMENTS

This invention will be described below as related to the embodiments, however it goes without saying that this invention is not limited to only such the embodiments.

EXAMPLE 1

In this example, CD's for computer software of sample Nos.1 to 4 and CD's for music of sample Nos. 5 and 6 were used as the transparent optical polymer molding 1 shown in FIG. 1A, and the shear flow patterns of the transparent polymer materials were observed in accordance with the method for visualizing the higher-order structure of the transparent optical polymer molding according to the first embodiment.

In this example, a black-light (main wavelength: 250~450nm) was used as the light source 11 in the incident optical system, and a filter transmissible to light of which wavelength is in a range of 300 to 400 nm was used as the incident-side filter 12.

On the other side, a filter transmissible to light with wavelength of 300 to 400 nm was used as the outgoing-side filter 13. The light $L_2$ with wavelength range of 300 to 400 nm selected through the outgoing-side filter 13 was formed in an image at the optical imaging system 14, was taken as the image in the image pickup device 15 and displayed by the image display device 17 after preparing the image in the image processing device 16.

Figure 4:
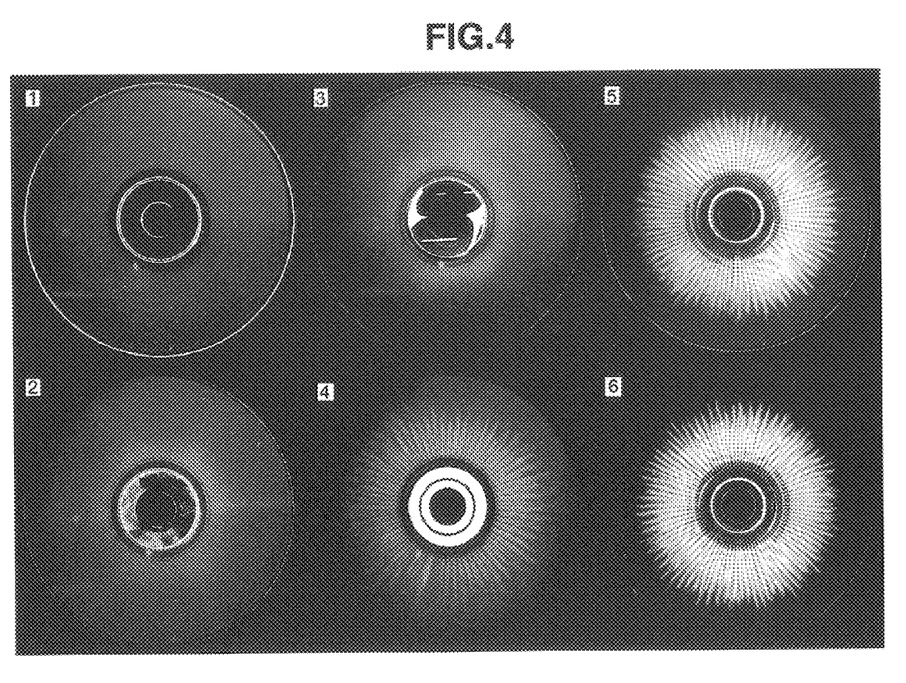
FIG. 4 is a photograph showing images as results of the visualizing test of the higher-order structure with respect to transparent optical polymer moldings (CD) of sample Nos.1 to 6 in the first example.

Consequently, the images were obtained with respect to the samples of Nos.1 to 6 as shown in FIG. 4, and it was confirmed that it is possible to visualize and observe the shear flow pattern of the transparent polymer materials.

EXAMPLE 2

In this example, a rectangular prism (orthogonal sides: 20 mm×20 mm, length (in the direction perpendicular to the surface of FIG. 5A): 35 mm) formed of polyolefine series resin through the injection moulding was used as the transparent optical polymer molding 1A shown in FIG. 2, and the shear flow pattern of the transparent polymer material developing in the region near to the injection gate of the prism (rectangular portion on the lower left side in FIG. 5A) was observed after magnification in a macroscopic level through the method for visualizing the higher-order structure of the transparent optical polymer molding according to the second embodiment. In this time, the light source 11 in the incident optical system, the incident-side filter 12, the outgoing-side filter 13 and the image pickup device 15 were the same as the apparatus used in the Example 1.

Figure 5A:
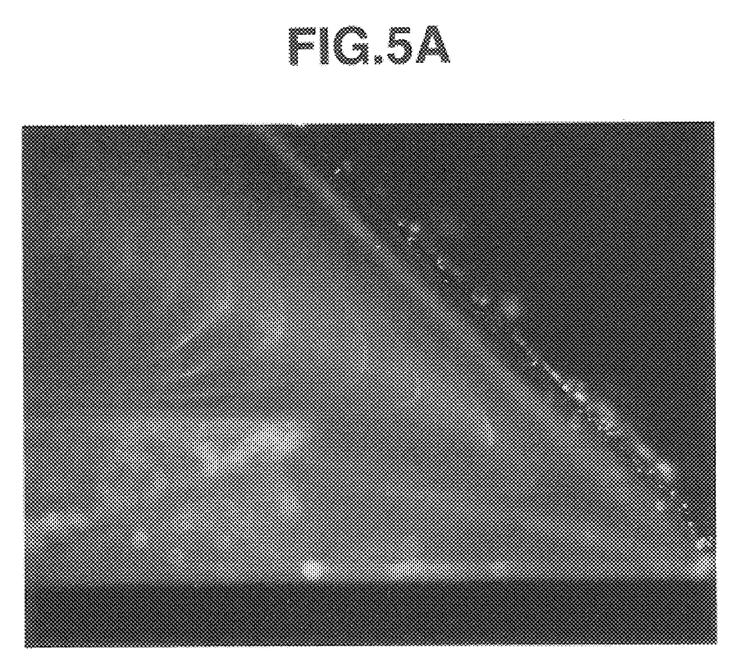
FIG. 5A is an image showing a result of the visualizing test of the higher-order structure with respect to a transparent optical polymer molding (rectangular prism) in the second example.
Figure 5B:
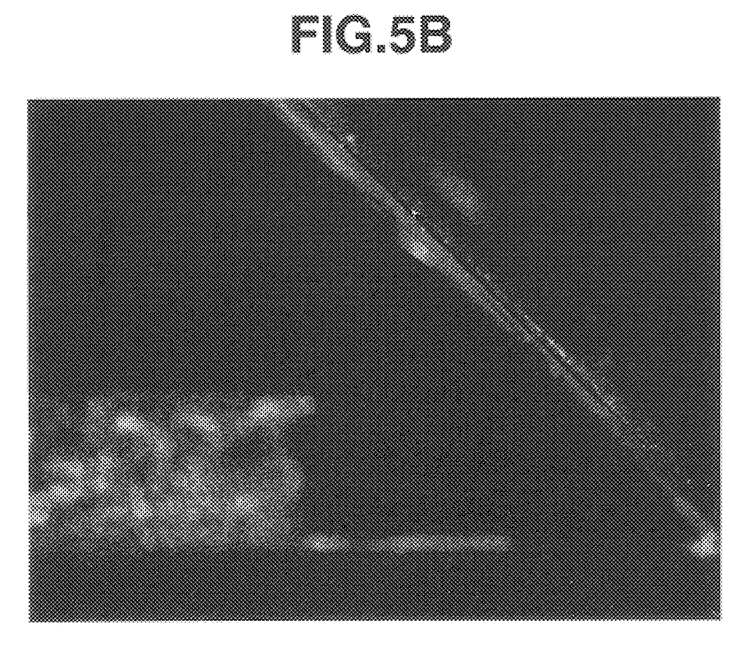
FIG. 5B is a comparative image by ordinary approach photographing of the rectangular prism in the second example.

In this case, although an image obtained by the ordinary approach photographing is shown in FIG. 5B for comparison, the picture image becomes rough because of a record under the optimum setting condition for the visualization method of the higher-order structure of the transparent optical polymer molding according to the second embodiment.

As is apparent from the picture images shown in FIGS. 5A and 5B, it was proved that it is possible to visualize and observe the shear flow pattern in the rectangular prism, which is not possible to observe in the image taken by the ordinary approach photographing, through the method for visualizing the higher-order structure of the transparent optical polymer molding according to the second embodiment.

EXAMPLE 3

In this example, a lightguide plate (one of optical parts, 30 mm×40 mm, thickness: 1~2.5 mm) formed of polycarbonate series resin through the injection moulding was used as the transparent optical polymer molding 1A shown in FIG. 2, and the shear flow pattern of the transparent polymer material developing at the thick-walled part in the region near to injection gate (position on the left side in FIG. 6A) of the lightguide plate was observed after magnification in the macroscopic level in accordance with the method for visualizing the higher-order structure of the transparent optical polymer molding according to the second embodiment. Also in this example, the light source 11 of the incident optical system, the incident-side filter 12, the outgoing-side filter 13 and the image pickup device 15 were the same as the Example 1.

Figure 6A:
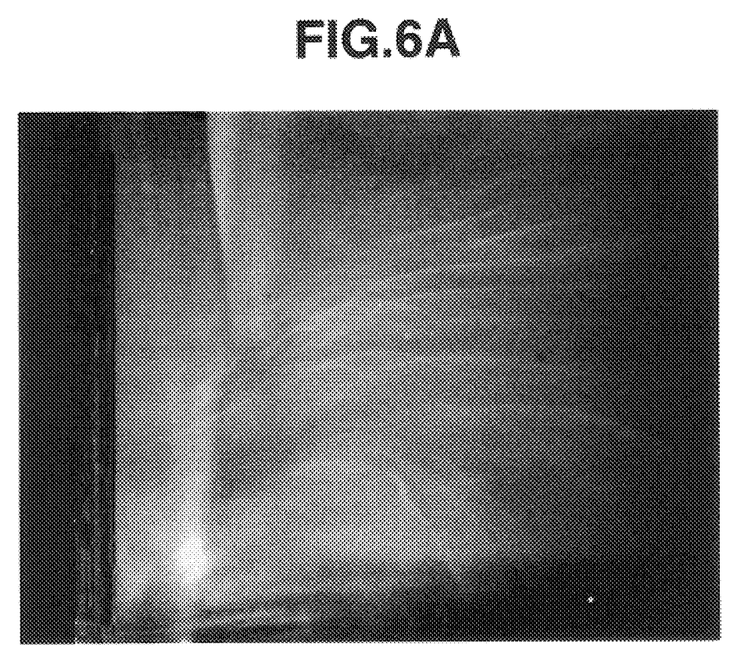
FIG. 6A is an image showing a result of the visualizing test of the higher-order structure with respect to a transparent optical polymer molding (lightguide plate) in the third example.
Figure 6B:
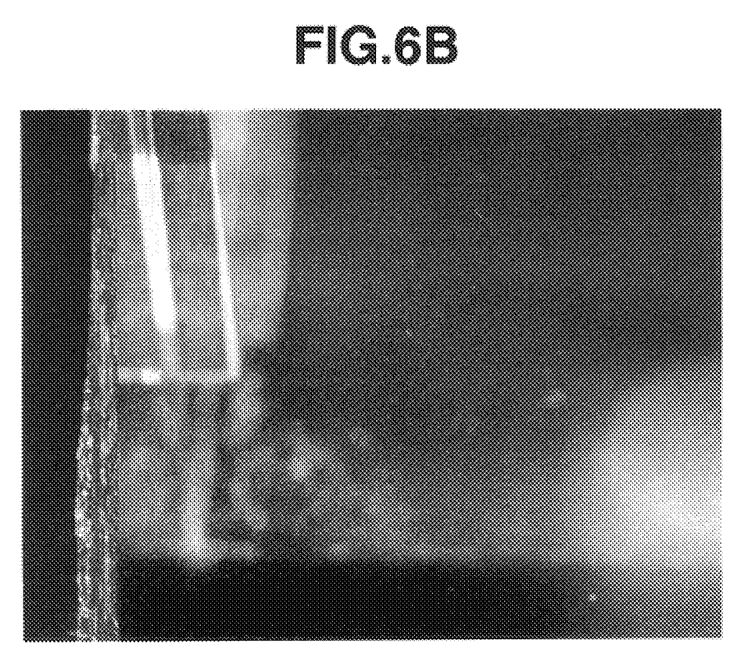
FIG. 6B is a comparative image by ordinary approach photographing of the lightguide plate in the third example.

Also in this case, an image obtained by the ordinary approach photographing is shown in FIG. 6B for comparison, however the picture image becomes rough because of a record under the setting condition optimum for the visualization method of the higher-order structure in the transparent optical polymer molding according to the second embodiment.

From the picture images shown in FIGS. 6A and 6B, it was proved that it is possible to visualize and observe the shear flow pattern in the lightguide plate, which is not possible to observe in the image obtained through the ordinary approach photographing, by applying the method for visualizing the higher-order structure of the transparent optical polymer molding according to the second embodiment.

EXAMPLE 4

In this example, two pickup lenses for CD (diameter: 4 mm, respectively) formed of PMMA series resin (a kind of acrylic resins) through the injection moulding in manufacturing conditions different from each other were used as the transparent optical polymer molding 1A shown in FIG. 2, and the shear flow patterns of the transparent polymer materials developing from the respective injection gates (positions on the lower sides in FIGS. 7A and 7B) of the pickup lenses were observed under magnification in the macroscopic level in accordance with the method for visualizing the higher-order structure of the transparent optical polymer molding according to the second embodiment of this invention. Also in this example, the light source 11 of the incident optical system, the incident-side filter 12, the outgoing-side filter 13 and the image pickup device 15 were the same as the Example 1.

Figure 7A:
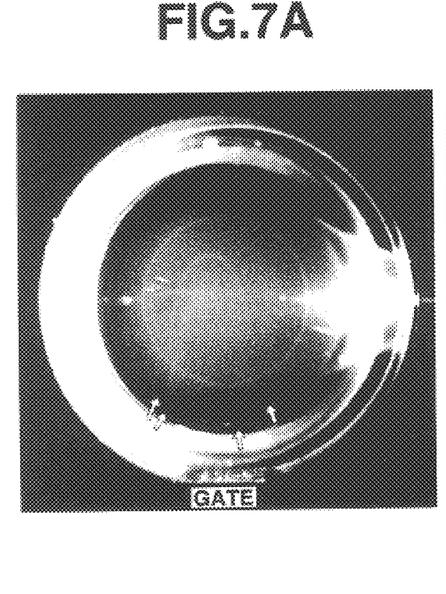
FIGS. 7A and 7B are images showing results of the visualizing test of the higher-order structure with respect to transparent optical polymer moldings (two pickup lenses for CD different from each other in manufacturing conditions) in the fourth example.
Figure 7B:
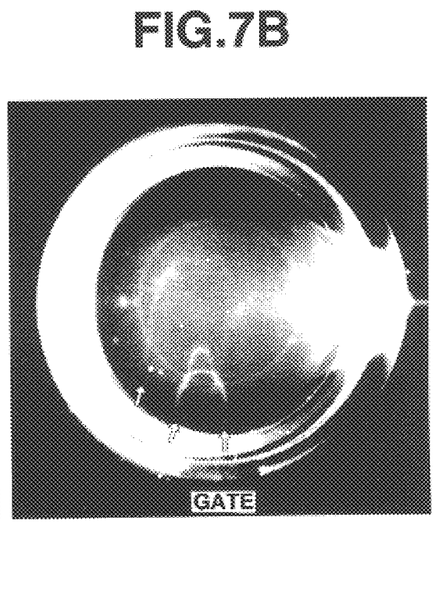

According to the picture images shown in FIGS. 7A and 7B, it was proved that it is possible to observe the shear flow patterns in the pickup lens by visualizing it through the method for visualizing the higher-order structure of the transparent optical polymer molding according to the second embodiment of this invention, and it was found that the parabolic distribution pattern of the shear flow was changed independent of the moulding condition as shown with arrows in FIGS. 7A and 7B.

EXAMPLE 5

In this example, the method according to this invention, which makes possible the non-destructive and non-contact observation of the higher-order structure, was applied to the observation of a section-prepared transparent optical polymer molding in advance. The above-mentioned pickup lens subjected is to the preparation of cross section was used as the transparent optical polymer molding 1A shown in FIG. 2, and the distribution of the shear flow on the section of the pickup lens was observed in accordance with the method for visualizing the higher-order structure of the transparent optical polymer molding according to the second embodiment of this invention. Also in this example, the light source 11 of the incident optical system, the incident-side filter 12, the outgoing-side filter 13 and the image pickup device 15 were the same as the Example 1.

Figure 8A:
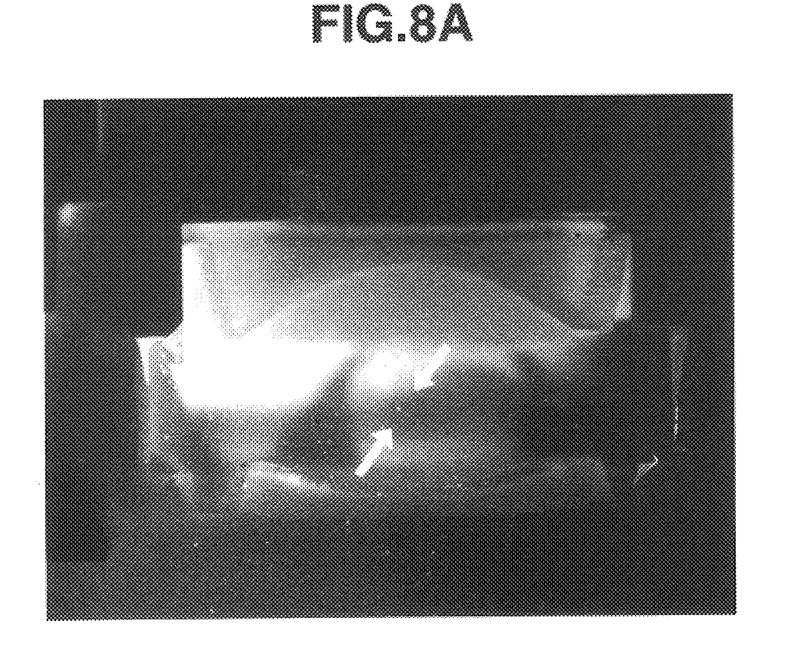
FIG. 8A is an image showing a result of the visualizing test of the higher-order structure with respect to a transparent optical polymer molding (section-prepared pickup lens for CD) in the fifth example.
Figure 8B:
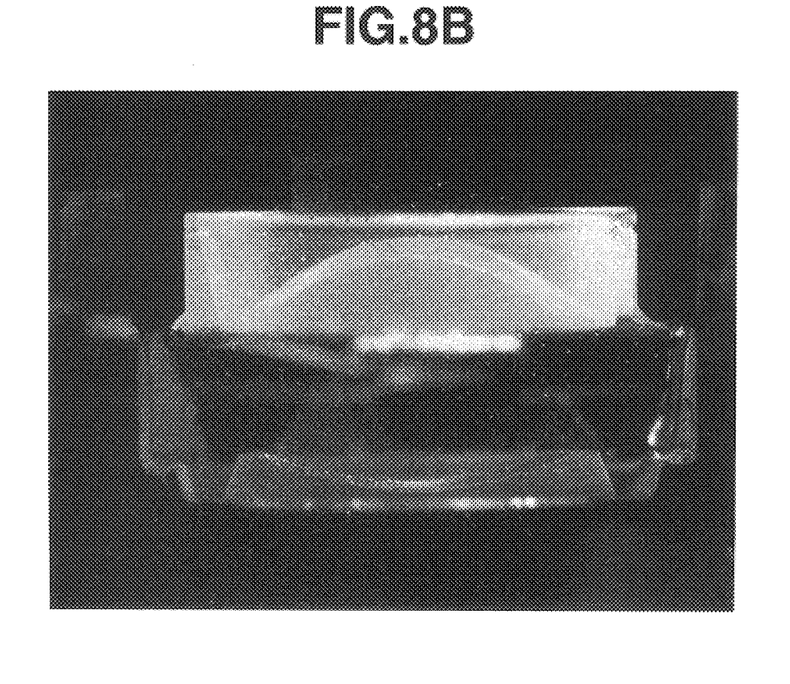
FIG. 8B is a comparative image by ordinary approach photographing of the pickup lens in the fifth example.

In this case, an image obtained by the ordinary approach photographing is shown in FIG. 8B for comparison.

As is apparent from the picture images shown in FIGS. 8A and 8B, it was proved that it is possible to visualize the shear flow distribution on the section of the pickup lens, which is impossible to visualize nor observe in the image taken by the ordinary approach photographing, and possible to observe it through the method according to the second embodiment of this invention, namely it was proved that it is possible to also apply the method for visualizing the higher-order structure of the transparent optical polymer molding according to this invention to the observation of the section in addition to the observation from the outside of the transparent optical polymer moldings. In this case, a white point existing between two arrows shown in FIG. 8A corresponds to one section of the parabola in the picture images shown in FIGS. 7A and 7B of the aforementioned example, therefore it was proved that it is possible to specify the position (distribution) of the shear flow in the direction of thickness of the lens by applying the visualization method of this invention to the section of the lens as shown in this example.

EXAMPLE 6

In this example, a base plate of DVD made of polycarbonate series resin was used as the transparent optical polymer molding 1 shown in FIG. 1, and the radial shear flow pattern existing in the region near to the center hole of the base plate of DVD was observed in accordance with the method for visualizing the higher-order structure of the transparent optical polymer molding according to the first embodiment of this invention.

In this example, two kinds of filters transmissible to light with wavelength of 200 to 400 nm and light with wavelength of more than 400 nm were used as the incident-side filter 12, and three kinds of filters transmissible to light with wavelength of less than 400 nm, light with wavelength of 400 to 800 nm and light with wavelength of more than 800 nm were used as the outgoing-side filter 13. In this manner, the radial flow pattern of the base plate was observed respectively under six kinds of conditions obtained by combining two incident-side filters 12 and three outgoing-side filters 13. Also in this example, the light source 11 of the incident optical system and the image pickup device 15 were the same as the Example 1.

Figure 9:
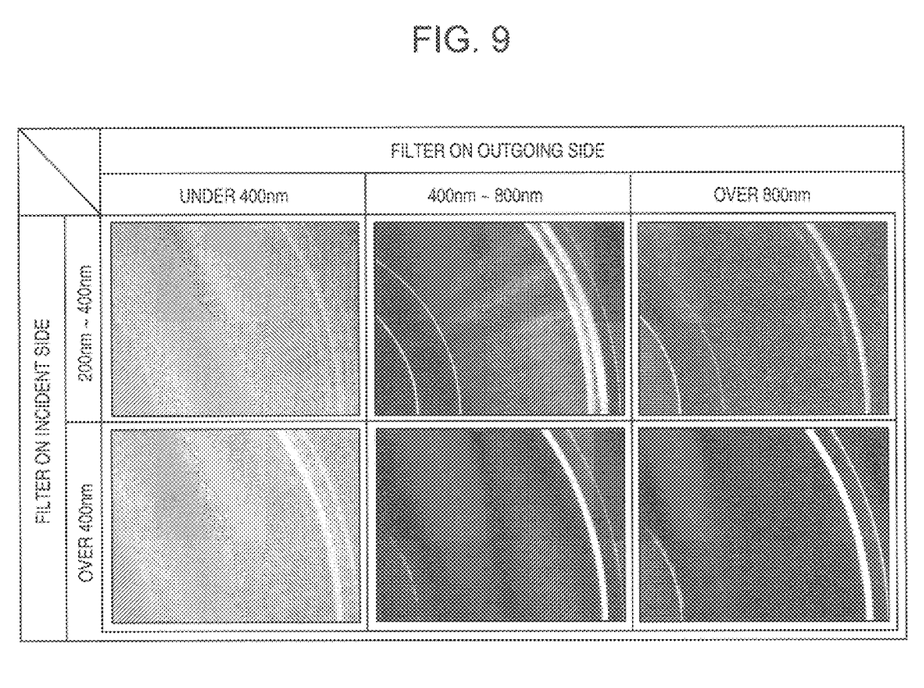
FIG. 9 is a photograph showing images as results of the visualizing test of the higher-order structure with respect to a transparent optical polymer molding (base plate of DVD) in the sixth example when the wavelength of the incident and outgoing side filters are changed respectively.

As a result, the picture images were obtained in the vicinity of the center hole of the base plate of DVD as shown in FIG. 9 and it was confirmed that it is possible to satisfactory visualize the radial shear flow pattern and possible to observe it by especially using the incident-side filter 12 transmissible to the light of which wavelength is in the range of 200 to 400 nm and the outgoing-side filter 13 transmissible to the light of which wavelength is in the range of 400 to 800 nm.

As explained above, in the method for visualizing the higher-order structure of the transparent optical polymer molding according to this invention, the light with the first specific wavelength is applied to the sample of the transparent optical polymer molding from the incident optical system, the light with the second specific wavelength is selected among the reflected wave and/or the transmitted wave of the light applied to the sample of the transparent optical polymer molding and visualized by the outgoing optical system. Therefore, an excellent effect can be obtained in that it is possible to visualize and observe the higher-order structure in the transparent optical polymer molding non-destructively and non-contactingly in the wide range of the microscopic level to the macroscopic level with respect to the large sample such as the CD and the DVD.

What is claimed is:

1. A method for visualizing higher-order structure of a transparent optical polymer molding comprising the steps of:
   applying light with a first specific range of wavelengths to the transparent optical polymer molding from an incident optical system; and
   visualizing light with a second specific range of wavelengths selected from reflected waves or transmitted waves of the light applied to said transparent optical polymer molding from the incident optical system by an outgoing optical system,
   wherein the first specific range of wavelengths and the second specific range of wavelengths are different from each other, and are selected to visualize higher order structure of the transparent optical polymer molding and thereby discern information regarding the structural integrity of the transparent optical polymer molding.

2. A method for visualizing higher-order structure of a transparent optical polymer molding as set forth in claim 1, wherein said transparent optical polymer molding is a product selected from the group consisting of a disc, a lens, a flat lens, a prism and an optical filter formed from a transparent resin.

3. A method for visualizing higher-order structure of a transparent optical polymer molding as set forth in claim 2, wherein said transparent resin is selected from the group consisting of polycarbonates, poly(ether sulfone), poly(ethylene terephthalate), polyolefine resins, acrylic resins, epoxy resins, and mixtures, alloys and composite materials of these resins.

4. A method for visualizing higher-order structure of a transparent optical polymer molding as set forth in claim 1, wherein said incident optical system is provided with a light source of ultraviolet rays or near ultraviolet rays.

5. A method for vitalizing higher-order structure of a transparent optical polymer molding as set forth in claim 4, wherein said light source is selected from the group consisting of a mercury lamp, an incandescent lamp, a black-light, a tungsten halogen lamp, a xenon lamp, an eximer UV lamp, and a UV laser.

6. A method for visualizing higher-order structure of a transparent optical polymer molding as set forth in claim 1, wherein said incident optical system is provided with an incident-side filter-to be passed through with light of which wavelength is not more than 400 nm.

7. A method for visualizing higher-order structure of a transparent optical polymer molding as set forth in claim 1, wherein said transparent optical polymer molding is supported on a plane directly.

8. A method for visualizing higher-order structure of a transparent optical polymer molding as set forth in claim 1, wherein said outgoing optical system is provided with an outgoing side-filter for selecting the light with the second specific range of wavelengths from the light reflected or transmitted from the transparent optical polymer molding, and said outgoing-side filter is passed through with light of which wavelength is in a range of 200 to 800 nm.

9. A method for visualizing higher-order structure of a transparent optical polymer molding as set forth in claim 1, wherein said outgoing optical system is provided with an optical imaging system, an image pickup device, an image processing device and an image display device.

10. A method for visualizing higher-order structure of a transparent optical polymer molding as set forth in claim 1, wherein said transparent optical polymer molding is supported on multiple points.

11. A method for visualizing higher-order structure of a transparent optical polymer molding as set forth in claim 1, wherein said transparent optical polymer molding is supported in a suspended state.

* * * * *